United States Patent
Moran

(10) Patent No.: US 6,621,081 B2
(45) Date of Patent: Sep. 16, 2003

(54) METHOD OF POLE TIP SAMPLE PREPARATION USING FIB

(75) Inventor: Timothy J. Moran, San Jose, CA (US)

(73) Assignee: International Business Machines Corporation, Armonk, NY (US)

(*) Notice: Subject to any disclaimer, the term of this patent is extended or adjusted under 35 U.S.C. 154(b) by 229 days.

(21) Appl. No.: 09/758,305

(22) Filed: Jan. 10, 2001

(65) Prior Publication Data

US 2002/0088947 A1 Jul. 11, 2002

(51) Int. Cl.⁷ .............................................. G01N 23/00
(52) U.S. Cl. ..................................................... 250/307
(58) Field of Search ............................... 250/307, 310, 250/309, 492.3

(56) References Cited

U.S. PATENT DOCUMENTS

| | | |
|---|---|---|
| 4,869,780 A | 9/1989 | Yang et al. |
| 5,270,552 A | 12/1993 | Ohnishi et al. |
| 5,472,566 A | 12/1995 | Swann et al. |
| 5,616,921 A | 4/1997 | Talbot et al. |
| 5,798,529 A | 8/1998 | Wagner |
| 5,804,460 A * | 9/1998 | Bindell et al. .............. 250/307 |
| 5,940,678 A | 8/1999 | Doong et al. |
| 5,990,478 A | 11/1999 | Liu |
| 6,042,736 A | 3/2000 | Chung |
| 6,067,703 A * | 5/2000 | Takahashi et al. ........ 29/603.13 |
| 6,111,724 A | 8/2000 | Santini |
| 6,146,797 A | 11/2000 | Fujii |
| 6,339,872 B1 * | 1/2002 | Chang et al. ............. 29/603.14 |

FOREIGN PATENT DOCUMENTS

| | | |
|---|---|---|
| JP | 6111749 | 4/1994 |
| JP | 9186210 | 7/1997 |

OTHER PUBLICATIONS

McCaffry and Barna, "Preparation of Cross–sectional TEM Samples", Microscopy Research and Technique, 1997, 36:362.

R. Alani, "Recent Advances in Ion Milling Techniques for TEM Specimen Preparation of Materials", International Symposium on Electron Microscopy, Beijing, China, Oct 22–23, 1990, pp. 461–478.

Kim, Jeong & Lee, "Minimization of differential thinning phenomena by using rocking–angle ion–milling to prepare thin films for cross–sectional tranmission electron microscopy", Ungyong Mulli (Korean Physical Society), Nov. 1997, vol. 10, No. 6, pp. 599–605.

K. Tsujimoto, et al., "Cross–sectional TEM Sample Preparation Method Using FIB Etching for Thin Film Transistor", Materials Research Society Symposium Proceedings vol. 480, 1997, pp. 207–215.

* cited by examiner

Primary Examiner—Bruce Anderson
(74) Attorney, Agent, or Firm—G. Marlin Knight

(57) ABSTRACT

The improved process according to the invention prepares samples for subsequent imaging by directing the FIB beam so that its incident angle is not parallel to the planar boundaries between the materials with different etch rates. This nonparallel alignment has the effect of evening out the etch rate, since most of the key beamlets cut more than one type of material. SEM images of the resulting samples are easier to interpret than those produced by the prior art since the obscuring effect of curtaining is reduced. This allows greater accuracy of measurement from the image obtained by an SEM. A method according to a preferred embodiment of the invention is used to prepare a pole piece tip of a magnetic transducer so that the bottom width may be more accurately measured.

15 Claims, 6 Drawing Sheets

METHOD OF POLE TIP SAMPLE PREPARATION USING FIB

FIELD OF THE INVENTION

The invention relates to the use of focused ion beams (FIB) in the preparation of samples comprising discrete regions of heterogeneous materials for viewing with electron microscopy and, more particularly, to the preparation of sections of magnetic heads for viewing with a scanning electron microscope (SEM).

BACKGROUND OF THE INVENTION

A typical prior art head and disk system is illustrated in FIG. 1. In operation the head 10 is supported by a suspension 13 as it flies above the disk 16. The magnetic transducer 10, usually called a "head," is composed of elements that perform the task of writing magnetic transitions (the write head 23) and reading the magnetic transitions (the read head 12). The electrical signals to and from the read and write heads 12, 23 travel along conductive paths 14 which are attached to or embedded in the suspension arm (not shown). Typically there are two electrical contact pads each (not shown) for the read and write heads 12, 23. Wires or leads (not shown) are connected to these pads and routed in the suspension 13 to the arm electronics (not shown). The disk 16 is attached to the spindle 22 that is driven by spindle motor 24 to rotate the disk. The disk 16 comprises a substrate 26 on which a plurality of thin films 21 are deposited. The thin films include ferromagnetic material that is used to record the magnetic transitions in which information is encoded.

The write head 23 portion of the transducer 10 is further illustrated in FIG. 2. FIG. 2 is a section view of the write head 23 taken parallel to the air bearing surface which is not shown. The write head 23 includes two pole pieces which are referred to as P1 31 and P2 32 and a coil (not shown). To decrease the side writing and, therefore, to reduce the track width, the pole pieces 31, 32 are shaped into narrow tips at the gap 33. To be effective the tip of P1 31 should be very close to the same size as the tip of P2 32 and should extend up from the larger body of P1 31 pole piece about 1 to 1.5 times the gap 33 thickness. In one prior art method P1 31 is deposited first and initially has a broad, flat tip that is subsequently ion milled using the tip of P2 32 as a mask to form the tip of P1 31. U.S. Pat. No. 6,111,724 to Hugo Santini discusses a prior art process for making P2 32 tips and describes an improvement using a zero—throat—height defining layer.

Regardless of the method used to form P2 32, the width of the track written by this type of inductive head 23 is largely determined by the width of the bottom of P2 32 (P2b). P2 32 tends to be wider at the top (away from the gap 33) which creates an additional complication in measuring the width of P2b. It is important to be able to measure P2b with some precision to monitor the manufacturing process. There are numerous variables in the process which affect the formation and shape of P2 32 including those affecting the photolithography used to define the shapes, the plating process used for depositing the ferromagnetic material, the seed layer removal process and the ion milling used to shape P1 31 using P2 32 as a mask. These variables can change from time to time in the manufacturing process and may even vary across a single wafer (not shown).

One prior art method used to measure the width of P2b uses a FIB to cut a section in the write head 23 to expose the tip of P2 32, the gap 33 and the tip of P1 31. In FIG. 2, a thin film layer of protective material 37 such as tungsten (W) or platinum (Pt) is deposited to preserve the P2 32 outline while a hole (not shown) is being cut. The hole is cut with a perpendicular incidence to expose the section illustrated in FIG. 2 as a substantially planar sidewall of the hole. An SEM beam is then used at an angle off of perpendicular to image the sidewall. The SEM image thus obtained will contain an image of the P2 32 and P1 31 tips. However, this prior art method is deficient in that it fails to yield truly planar side walls since the different materials that make up the sample of the pole piece tips have significantly different FIB etch rates. For example, the head fabrication process typically creates a thin redep layer (not shown) on the sides of P2 32 which has a higher etch rate than the NiFe which is commonly used for pole piece tips and the tungsten protective material has a lower etch rate than the NiFe. Voids in the tungsten can also contribute to variations in etch rate. Since the FIB has a very small diameter and is rastered, the higher etch rate materials will be cut deeper and the surface will not be planar. This topography can contribute to undesirable contrast. In the samples of pole piece tips, the top of the P2 32 is several microns higher than the surrounding field region. Since the beam begins to cut on the field at the same time as the top of P2, the field region will be greatly recessed relative to the P2 32. Therefore, the ending surface will have nonplanarity which follows the P2 pattern. The nonplanarity of the cut surface obscures contrast in the SEM image at the boundary between the different materials (for example, NiFe and the W) that define the critical dimension to be measured. The nonplanarity introduces undesirable contrast that makes it difficult to measure contrast due to the boundaries between the NiFe P2 32 and the tungsten coating 37 in the SEM image. Since the width of the NiFe P2 32 is a critical dimension, it is important to be able to measure it precisely.

Thus, there is a need for an improved process for preparing the pole piece tip samples for imaging.

SUMMARY OF THE INVENTION

The improved process according to the invention prepares samples for imaging by directing the FIB beam so that its incident angle is not parallel to the planar boundaries between various materials including boundary between the protective material deposited over the structure and outside material of the structure. This has the effect of evening out the etch rate, since the majority of the key beamlets cut more than one type of material. The resulting sample surface is easier to interpret than one produced by the prior art since the obscuring effect of curtaining is reduced. This allows greater accuracy of measurement from the image obtained by an SEM. A method according to a preferred embodiment of the invention is used to prepare a P2 tip so that the bottom width may be more accurately measured. A sample magnetic transducer with the P2 tip exposed is prepared for imaging by first depositing a protective material such as tungsten or platinum over the P2 tip (which is a ferromagnetic material such as NiFe). The sides of P2 tip and the protective material have contact planes which are perpendicular to the general plane of the upper surface of the sample. The sample is positioned in relation to the focused-ion beam so that most of the key beamlets cut at least two materials, for example, tungsten and NiFe, in the planar contact region to reduce the curtaining effect caused by the unequal rates of etching. The focused-ion beam is then used to etch away material to expose a new surface on which the cross section of the P2 tip is exposed for subsequent imaging.

DETAILED DESCRIPTION OF THE INVENTION AND THE PREFERRED EMBODIMENTS

Figure 1:
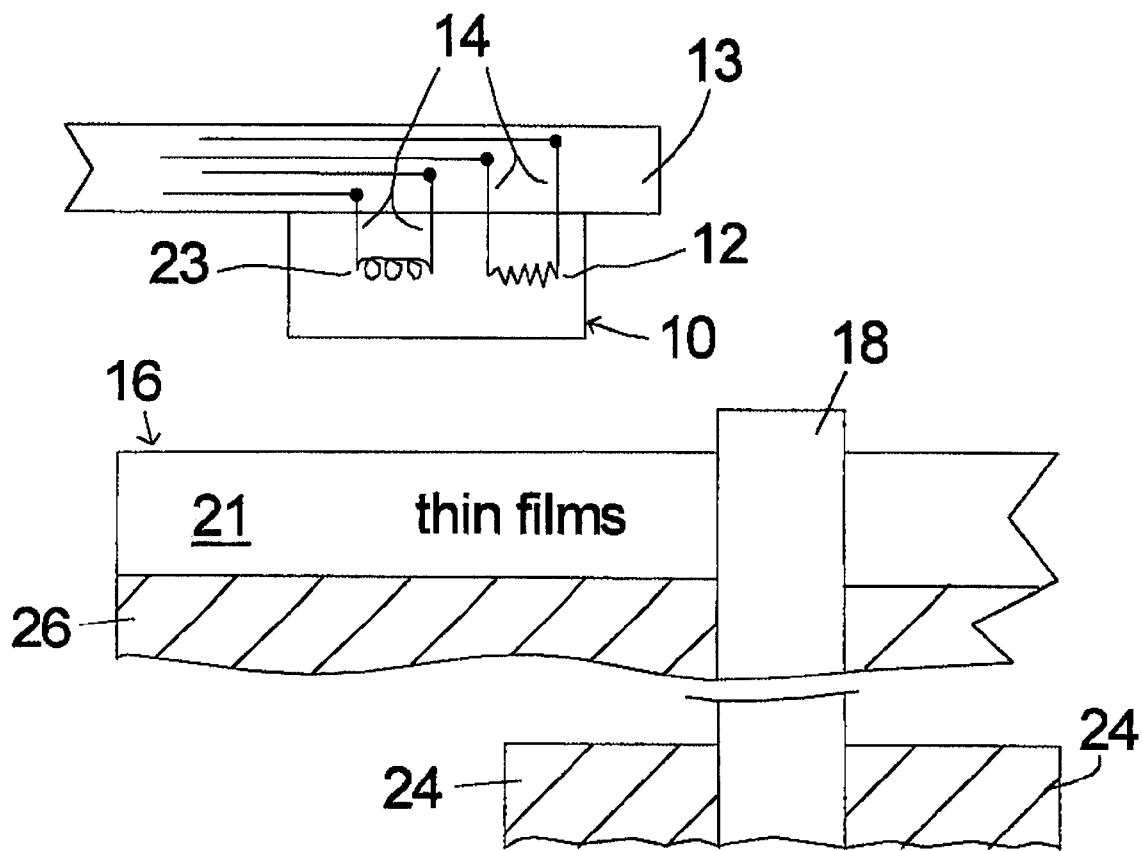
FIG. 1 is an illustration of the structure of a prior art disk drive having a write head on which the method of the invention can be used.
Figure 2:
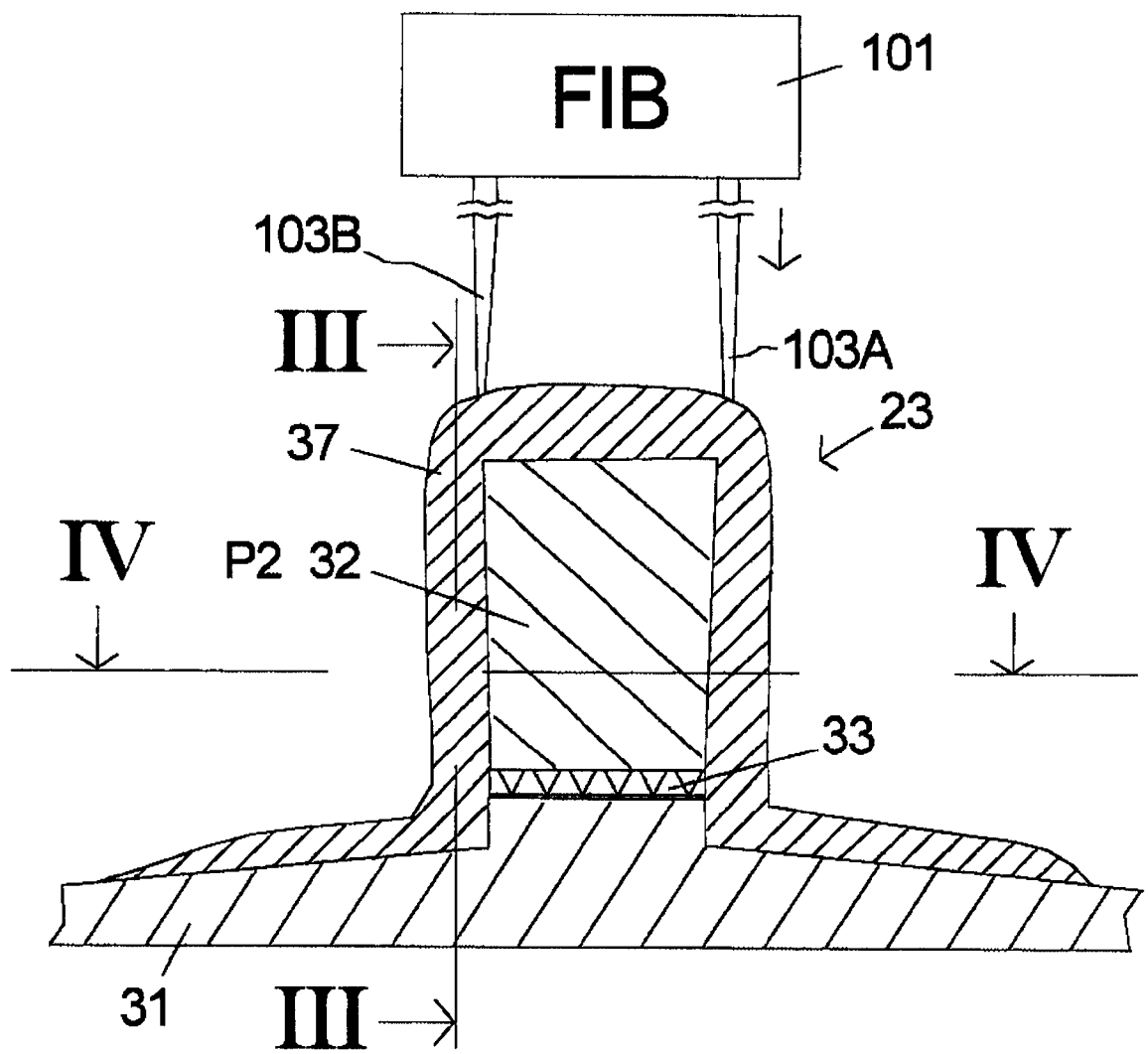
FIG. 2 is an illustration of the prior art technique of preparing a P2 tip sample using a focused-ion beam which shows a section of a sample magnetic transducer taken parallel to the air bearing surface.

In order to describe a preferred embodiment of the method of the invention, additional details of the prior art method and its deficiency will be given. In FIG. 2 the prior art process is illustrated. The write head 23 is shown in a sectional view taken parallel to the air bearing surface which is not shown. The target is more particularly the bottom of the tip of P2 32 which confronts the gap 33. The tip of P1 31 confronts the opposing side of the gap 33. In this view the protective material 37 has been deposited on the surface of the sample transducer. This is conventionally done using the FIB 101. Platinum and tungsten are the two most common materials used for this purpose. The size of the P2 tip 32 structure is on the order of one micron wide. The sample 23 is positioned according to the prior art teaching so that focused-ion beam 103A is incident upon the P2 tip 32 substantially perpendicular to the surface of the sample 23. This means that the focused-ion beam 103A is incident parallel to the contact surface between the protective material 37 and the sides of the P2 tip 32. Since the FIB is rastered, it moves across the P2 tip 32 as is illustrated by the position of the beam 103B shown in phantom. The beam is extremely small in relation to the structures in the write head 23. The size has been exaggerated for illustration purposes in the figures. The FIB device 101 is very far away from the P2 tip 32 when viewed in the scale of the head structures and, therefore, strikes the head sample at an essentially constant angle despite being rastered.

Figure 3:
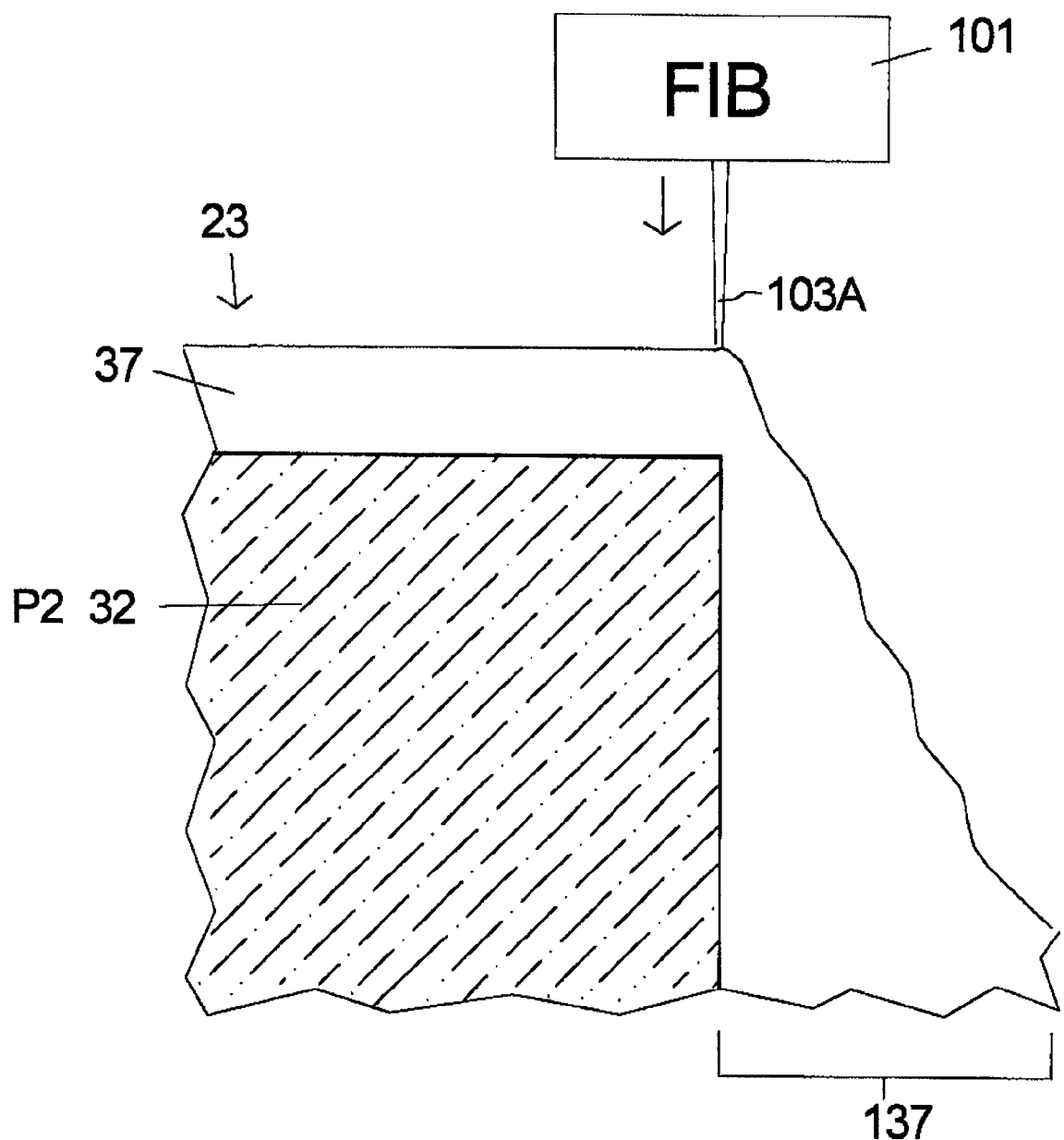
FIG. 3 is an illustration of the prior art technique of preparing a P2 tip sample using a focused-ion beam which shows a section of a sample magnetic transducer taken along the IIII—IIII line in FIG. 2.

FIG. 3 is a section of the head sample 23 shown in FIG. 2 as taken along the line marked as III—III. This view shows the curtaining 137 of the protective material 37. The curtains 137 become progressively thicker the farther they are away from the surface. The P2 tip 32 is shown only in phantom in this view since it is not actually present in this section. Since it is the bottom of the P2 tip 32 which is most critical to measure, the curtaining 137 greatly complicates the interpretation of the SEM image.

Figure 4:
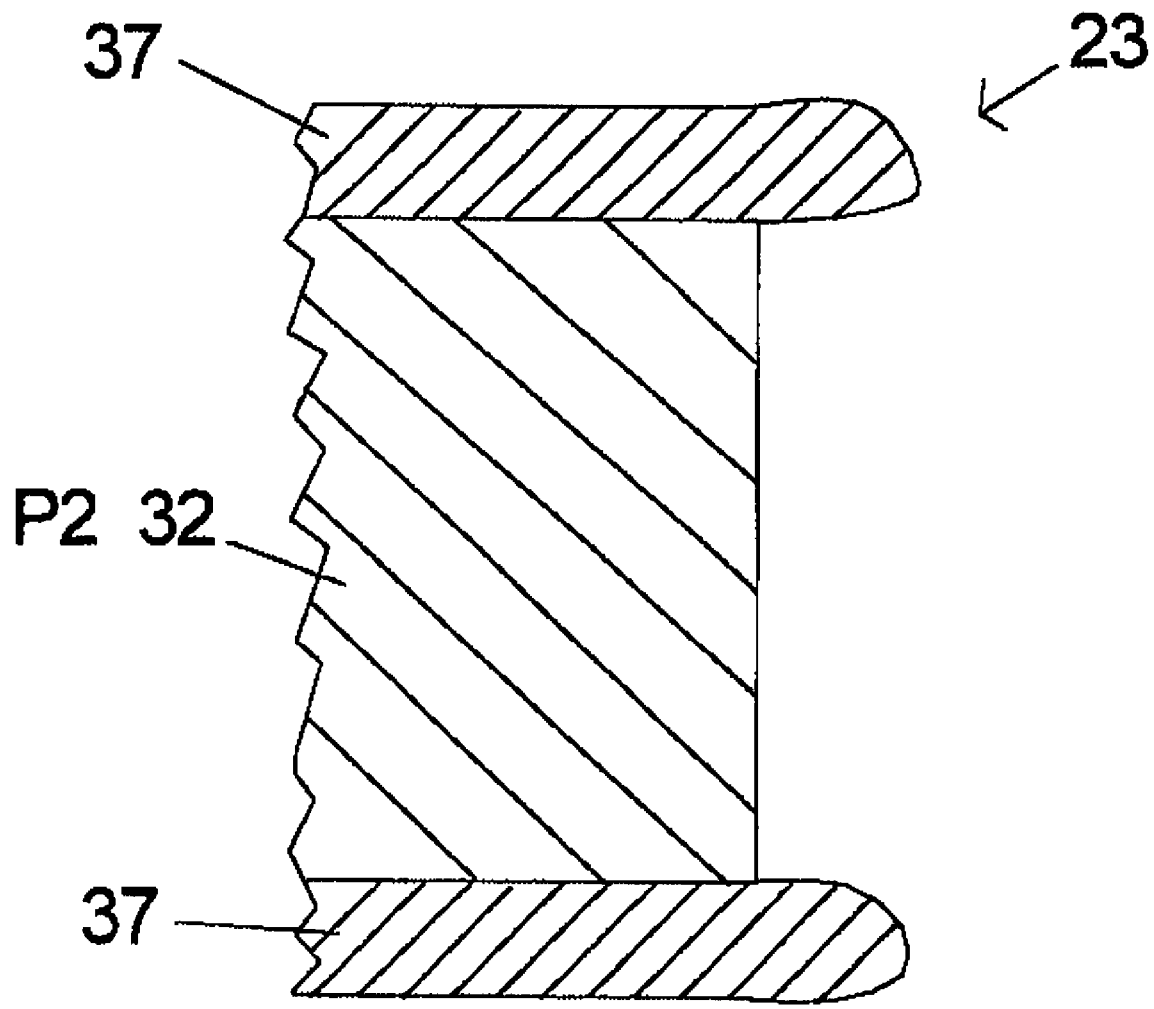
FIG. 4 is an illustration of the prior art technique of preparing a P2 tip sample using a focused-ion beam which shows a section of a sample magnetic transducer taken along the IV—IV line in FIG. 2.

FIG. 4 is a section of the head sample 23 shown in FIG. 2 as taken along the line marked as IV—IV. This view shows the curtaining 137 of the protective material 37 in a plan view. The surface of the P tip 32 is recessed back from the front edge of the curtains 137 due to the higher etch rate of the material typically used for pole piece tips in magnetic transducers (NiFe or a similar ferromagnetic material).

Figure 5:
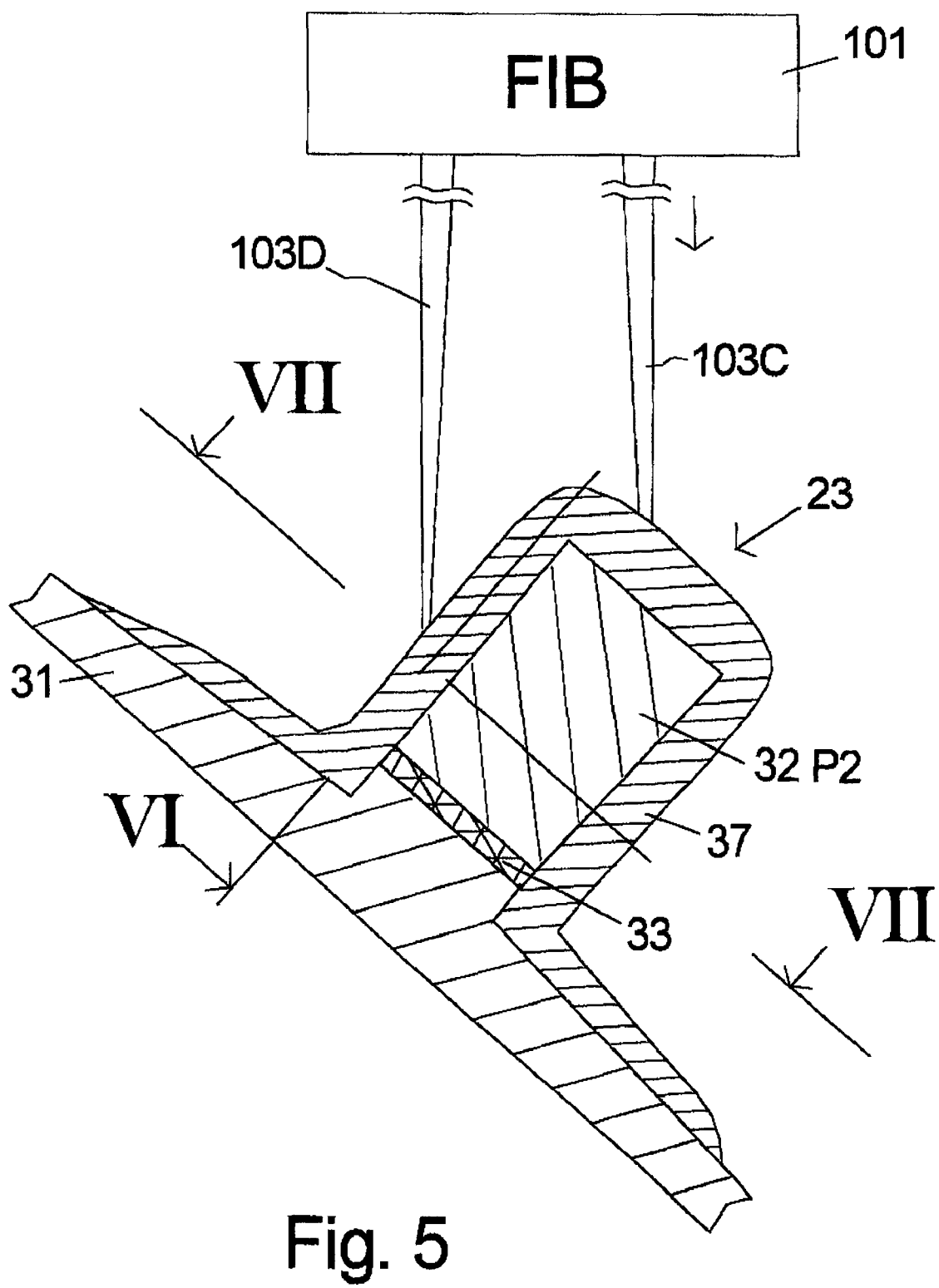
FIG. 5 is an illustration of a method, according to the invention, of preparing a P2 tip sample using a focused-ion beam which shows a section of a sample magnetic transducer taken parallel to the air bearing surface.
Figure 6:
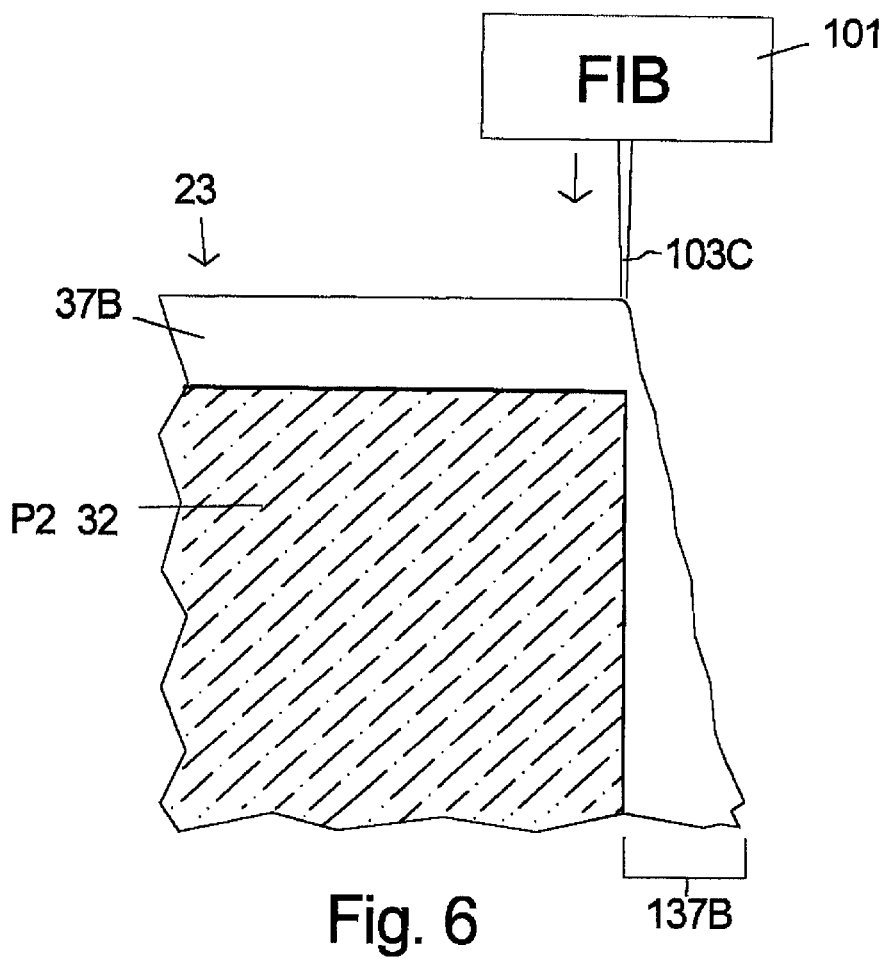
FIG. 6 is an illustration of a method, according to the invention, of preparing a P2 tip sample using a focused-ion beam which shows a section of a sample magnetic transducer taken along the line VI—VI in FIG. 5.
Figure 7:
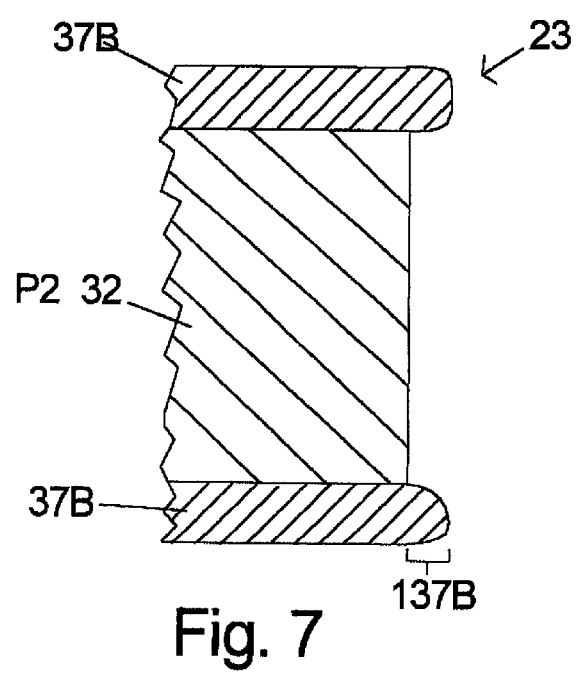
FIG. 7 is an illustration of a method, according to the invention, of preparing a P2 tip sample using a focused-ion beam which shows a section of a sample magnetic transducer taken along the line VII—VII in FIG. 5.

The method according to the invention improves on the prior art by reducing the curtaining effects and thereby allowing more precise imaging and measurement to be performed. FIG. 5 illustrates the invention. It shows a section taken parallel to the air bearing surface (not shown). As in the prior art method the protective material 37 is deposited over the exposed P2 tip 32, gap 33 and the tip of P1 31. The incident angle of the focused-ion beam 103C is altered by positioning the sample 23 at a non-perpendicular angle to the beam 103C and the rastered position 103D shown in phantom. An angle on the order of 45 degrees is preferred. The effect is to cause the majority of the key beamlets to be cutting both the protective material and the NiFe. The applicant has discovered that this reduces the curtaining. Note that in the FIG. 2 illustration of the prior art certain beamlets will be cutting only the protective material 37 which increases the curtaining of the protective material 37. The improved results achieved by the method according to the invention are further illustrated in FIG. 6 which shows a section taken along the line VI—VI of FIG. 5. The curtaining 137B is significantly reduced from that of the prior art method. The reduction of the curtaining is further illustrated in FIG. 7 which shows a section taken along the line VII—VII of FIG. 5. The distance that the exposed P2 tip 32 face is recessed back from the front edges of the curtains 137B is shown to be reduced over that of the prior art method.

An additional advantage of the method of the invention is that it alleviates the type of nonplanarity mentioned above which is due to the beam cutting the surrounding field at the same time as the top of P2 32. Using the method of the invention, the recession of the field region will be reduced relative to P2 32.

The invention has been described as used to prepare a sample P2 tip in an inductive write head for imaging, but the utility of the method for other similar features will be apparent to those skilled in the art which will nevertheless be with the spirit and scope of the invention.

What is claimed is:

1. A method of using a focused-ion beam to prepare a sample of a structure including a feature of a magnetic transducer for subsequent imaging, the structure being disposed above a surrounding area on an upper surface of the sample, the sample having first and second materials in contact at a planar internal interface which is perpendicular to the upper surface of the sample, the first material and the second material having unequal rates of etching when exposed to the focused-ion beam, the method comprising the steps of:

positioning the upper surface of the sample at a non-perpendicular angle to an incident angle of the focused-ion beam so that a majority of beamlets of the focused-ion beam cut first and second materials at the planar internal interface to reduce a curtaining effect from the unequal rates of etching; and etching away first and second materials using the focused-ion beam to form a new surface of the structure for subsequent imaging, the planar internal interface intersecting the new surface as a line.

2. The method of claim 1 wherein the first material is a protective material deposited over the structure of the magnetic transducer.

3. The method of claim 2 wherein the protective material is tungsten.

4. The method of claim 2 wherein the protective material is platinum.

5. The method of claim 1 wherein the first or second material is ferromagnetic.

6. The method of claim 2 wherein the structure is a pole piece tip.

7. The method of claim 6 wherein the pole piece tip has a rectangular cross section as viewed from an air bearing surface of the magnetic transducer and two sides of the pole piece tip are substantially perpendicular to the plane of the upper surface of the sample.

8. The method of claim 7 further comprising the step of imaging the new surface using an SEM.

9. The method of claim 8 further comprising the step of measuring a dimension of the pole piece.

10. A method comprising the steps of:

using a focused-ion beam to deposit a protective material over a pole piece tip on a surface of a magnetic transducer, the pole piece tip having first and second planar surfaces which are perpendicular to the surface of the magnetic transducer, the protective material having a lower etch rate when exposed to the focused-ion beam than an etch rate of a material of the first planar surface of the pole piece tip;

positioning the first and second planar surfaces at a non-zero angle in relation to the focused-ion beam; and cutting away material in the structure using a rastered focused-ion beam with a majority of beamlets cutting the protective material and the pole piece tip to reduce curtaining and to expose a sample planar surface of the pole piece tip for subsequent imaging, the sample planar surface being perpendicular to the first planar surface of the structure.

11. The method of claim 10 wherein the protective material is tungsten.

12. The method of claim 10 wherein the protective material is platinum.

13. The method of claim 10 wherein the pole piece tip has a rectangular cross section as viewed from an air bearing surface of the magnetic transducer and two sides of the pole piece tip are substantially perpendicular to the surface of the magnetic transducer.

14. The method of claim 10 further comprising the step of imaging the new planar surface using an SEM.

15. The method of claim 14 further comprising the step of measuring a dimension of the pole piece.

* * * * *